US005124490A

United States Patent [19]
Cipullo

[11] Patent Number: 5,124,490
[45] Date of Patent: Jun. 23, 1992

[54] REMOVAL OF ACIDS FROM PHENOL USING ANIONIC EXCHANGE RESINS

[75] Inventor: Michael J. Cipullo, Mt. Vernon, Ind.

[73] Assignee: General Electric Company, Mt. Vernon, Ind.

[21] Appl. No.: 715,955

[22] Filed: Jun. 17, 1991

[51] Int. Cl.$^5$ .............................................. C07C 37/70
[52] U.S. Cl. ................................... 568/758; 568/724; 568/748; 568/749; 568/753; 568/755
[58] Field of Search .............. 568/749, 753, 758, 724, 568/748, 755

[56] References Cited

U.S. PATENT DOCUMENTS 4,327,229  4/1982  Mendiratta .......................... 568/758

FOREIGN PATENT DOCUMENTS 1239701  5/1967  Fed. Rep. of Germany ...... 568/758
718467  11/1954  United Kingdom ................ 568/758

*Primary Examiner*—Warren B. Lone
*Attorney, Agent, or Firm*—Martin B. Barancik; Joseph T. Eisele

[57] ABSTRACT

Acid contaminants leached from acidic ion-exchange resins and carried in process streams with phenol are separated from the phenol by passing the process stream in contact with an anionic exchange resin, whereby the acid contaminants react with and bond to the anionic exchange resin.

3 Claims, No Drawings

REMOVAL OF ACIDS FROM PHENOL USING ANIONIC EXCHANGE RESINS

BACKGROUND OF THE INVENTION

1. Field of the Invention

The invention relates to methods of purifying phenol, and more particularly to the removal of acid contaminants from phenol using anionic exchange resins.

2. Brief Description of the Related Art

Phenol is a starting reactant for the synthesis of a wide variety of chemical compounds including, for example, bisphenol-A. In the synthesis of such compounds, purity of the phenol is generally a concern. For example, in the synthesis of bisphenol-A, contaminant acid compounds present in association with the phenol can have an adverse effect when carried into the product bisphenol-A (high temperature cracking of the bisphenol-A). The contaminants can catalyze numerous side reactions and degrade the desired product.

The use of anionic exchange resins to remove acidic contaminants from phenol-containing process streams has been described previously. For example, European Patent Application 0 329 075 published Aug. 23, 1989 (Mitsui Toatsu Chemicals, Inc.) describes bisphenol-A product streams containing residual phenol reactant and acid contaminants. The product stream is treated with weakly basic ion-exchange resins to remove the acid contaminants before separating the desired bisphenol-A by distillation. A similar treatment of bisphenol-A product streams is described in U.S. Pat. No. 4,766,254 (Faler et al.).

The present invention is concerned with purity of phenol as a starting material in organic synthesis and not with the treatment of other products which may be contaminated with phenol, i.e.; the phenol being present only as a contaminant itself.

SUMMARY OF THE INVENTION

The invention comprises a method of removing acidic contaminants from a process stream consisting essentially of phenol and said acidic contaminants, which comprises; reacting the acidic contaminants with an anionic exchange resin; and separating the resulting reaction mixture from the resin, whereby phenol is obtained free of the acidic contaminants.

The separated reaction mixture comprises phenol, substantially free of the acid contaminants and useful, for example, as a reactant in the synthesis of high quality bisphenol-A. Observations of the purified phenol have suggested that unwanted color bodies in the crude starting mixture may also be removed.

DETAILED DESCRIPTION OF THE PREFERRED EMBODIMENTS OF THE INVENTION

Phenol is frequently recovered from reaction mixtures resulting from the condensation of a molar excess of phenol with acetone in the presence of acidic ion-exchange resins. The recovered phenol may be contaminated with small quantities (2 to 200 PPM) of low molecular weight sulfonic acids or oligomers leached from the acidic ion-exchange resin catalysts. Additionally, fresh phenol may be contacted with an acid ion exchange resin during the start up or a periodic shutdown of a process that makes a bisphenol such as bisphenol-A by condensation over such acidic ion exchange resin. We have found that surprisingly a major amount of leaching occurs during these non-reaction time periods. Such leaching brings out sufficient impurities that the phenol contacting the ion exchange resin is no longer suitable for use as a reactant in the ensuing condensation reaction with a ketone, particularly acetone. Such problems of potential cracking of the bisphenol during high temperature steps and intense color in the final product are some of the problems encountered. An objective of the present invention is to remove such acid contaminants from the phenol, so that the phenol can be re-used in processes where the contaminant acids would have an adverse effect.

The method of the invention comprises treating the contaminated phenol by passing it over an anionic exchange resin, thereby reacting the acid contaminants with the resin and removing them from the phenol.

The ion exchange resins useful in the method of this invention include all known basic resins of this type. For the most part, they are amine or quaternary ammonium resins typically containing such moieties as dimethylbenzylamino groups or corresponding methyl-quaternized groups attached to a polymer chain. Amine resins including those having a pyridyl group are often preferred. For the purpose of the invention, the amine resins are employed in the free base form, although quaternary resins wherein the counterion therein is a hydroxide anion can also be used.

Methods of preparing anionic exchange resins are generally well known; see for example the method described in U.S. Pat. No. 2,632,001 (McMasters et al.) incorporated herein by reference thereto. This method comprises the side-chain chlorination of poly(vinyltoluene), followed by reaction with a tertiary amine in the presence of a polar solvent such as water to form a quaternary ammonium salt. Representative of commercially available resins of this type are Amberlite IRA-400, Amberlite IRA-401, Amberlite IRA-402, Amberlite IRA-900, Duolite A-101-D, Duolite ES-111, Dowex 1, Dowex 11, Dowex 21K, and Ionac A-540 and those derived from dimethylethanolamine $CH_3)_2$—$NCH_2CH_2OH$, Amberlite IRA-410, Amberlite IRA-911, Dowex 2, Duolite A-102-D, Ionac A-542, and Ionac A-550 (Amberlite, Duolite, Dowex and Ionac are registered U.S. trademarks).

Preferred for use in the present invention are weak-base anionic exchange resins, containing primary, secondary and tertiary amine groups. Commercially available examples of these products are Amberlite A-21, Dowex 44, Duolite A-7, Ionac A-260, Amberlite IRA-35, Amberlite IRA-68 (the latter two resins are gelular with acrylic backbones) and Reillex-402, a polyvinyl pyrridine from Reilly Industries, Inc.

Contact between the phenol/acid contaminant mixture and the anion exchange resin may be effected by any convenient means. It is generally preferred to pass the phenol mixture for purification through a column containing the resin, at temperatures in the range of about 45°–125° C. and preferably about 50°–75° C. Passage of the phenol mixture through the column may be upward or downward, for a time sufficient to remove the acidic contaminants.

Upon contact with the anion exchange resin, acidic impurities are removed by salt formation therewith. Separation of the reacted resin from the desired phenol may be accomplished by conventional procedures, i.e.; decantation, filtration and like procedures. When the resin has been exhausted it may be regenerated, for example by treatment with a 6 to 10 percent caustic aqueous base. Such treatment can be preceded by washing with liquid phenol, to remove phenol soluble impurities whose presence would decrease the efficiency of the resin or regenerated, followed by a water wash.

According to the process of the present invention, the treatment of the phenol/acid contaminant mixture with the weakly basic ion-exchange resin may be carried out continuously or batchwise. Generally, the lower the flow rate, the greater the effective efficiency of the removal of the acidic contaminants. For continuous treatment, the phenol mixture is preferably fed at a flow rate of 2 to 1000 kg/hr for 1 kg of the weakly basic ion-exchange resin, preferably 3-50. For batchwise treatment, the phenol mixture is preferably mixed with 1 to 20 wt % of the weakly basic ion-exchange resin, for 5 to 60 minutes.

The following example and preparations describe the manner and process of making and using the invention and set forth the best mode contemplated by the inventor of carrying out the invention but are not to be construed as limiting the invention. cl EXAMPLE A mixture of phenol and acidic impurities including low molecular weight acid oligomer impurities is treated by passage in contact with an anionic exchange resin (millequivalency of 5.0; A-21, a macrorecticular anionic exchange resin with a styrene backbone and functional $R-N(CH_3)_2$ groups; Rohm and Haas Co.). The mixture is continuously cycled at a temperature of circa 50° C. in a loop containing the bed of anionic resin (2482 lbs. of dry resin; 4 meters$^3$ volume) as well as acid ion exchange resin in a separate vessel. Volume of the phenol treated was slightly over 100,000 gallons. The following data reflect the diminishing presence of acid contaminants at the inlet and outlet of the anionic bed over time, with 0 hours indicating conditions at process initiation.

| TIME (HRS) | PHENOL FLOW RATE (M$^3$/HR) | PPM ACID BED INLET | ACID CONTAMINANTS OUTLET |
|---|---|---|---|
| 0 | 32 | 31 | 15 |
| 10 | 42 | 24 | 17 |
| 11.5 | 42 | 20 | 17 |
| 37.0 | 48 | 12 | 11.5 |
| 66.0 | 48 | 9 | 4 |

What is claimed is:

1. A method of removing acidic contaminants from phenol in a process stream resulting from the presence of acid ion-exchange resins, and which comprise low molecular weight sulfonic acids and oligomers, which comprises;

reacting the acidic contaminants with an anionic exchange resin; and separating the resulting reaction mixture from the anionic exchange resin, whereby phenol is obtained free of the acidic contaminants.

2. The method according to claim 1 wherein the anionic resin is weakly basic.

3. The method according to claim 1 wherein the anionic ion exchange resin is a resin having an amine or pyrridine functionality.

* * * * *